United States Patent
Mantanus et al.

(10) Patent No.: US 10,682,228 B2
(45) Date of Patent: Jun. 16, 2020

(54) METHOD AND APPARATUS FOR COMPRESSING/LOADING STENT-VALVES

(71) Applicant: Symetis SA, Ecublens (CH)

(72) Inventors: Luc Mantanus, Lausanne (CH); Fabien Lombardi, Prilly (CH); Pierre Simonin, Montflovin (FR); Youssef Biadillah, Geneva (CH); Jean-Luc Hefti, Cheseaux-Noreaz (CH); Stephane Delaloye, Bulach (CH)

(73) Assignee: Symetis SA, Ecublens (CH)

( * ) Notice: Subject to any disclaimer, the term of this patent is extended or adjusted under 35 U.S.C. 154(b) by 0 days.

(21) Appl. No.: 16/371,214

(22) Filed: Apr. 1, 2019

(65) Prior Publication Data
US 2019/0290427 A1    Sep. 26, 2019

Related U.S. Application Data

(63) Continuation of application No. 15/022,525, filed as application No. PCT/EP2014/069696 on Sep. 16, 2014, now Pat. No. 10,245,145.

(30) Foreign Application Priority Data

Sep. 16, 2013   (EP) .................................... 13184650

(51) Int. Cl.
*B23P 19/02* (2006.01)
*A61F 2/24* (2006.01)
(Continued)

(52) U.S. Cl.
CPC .......... *A61F 2/2436* (2013.01); *A61F 2/2418* (2013.01); *A61F 2/97* (2013.01);
(Continued)

(58) Field of Classification Search
CPC . B23P 17/00; B23P 11/00; B23P 19/02; B23P 19/12; A61F 2/00; A61F 2002/0072
See application file for complete search history.

(56) References Cited

U.S. PATENT DOCUMENTS 5,672,169 A    9/1997 Verbeek
5,893,867 A    4/1999 Bagaoisan et al.
(Continued)

FOREIGN PATENT DOCUMENTS

EP    2520251 A1   11/2012
WO   2010014834 A1    2/2010
(Continued)

OTHER PUBLICATIONS

International Search Report and Written Opinion dated Mar. 17, 2015 for International Application No. PCT / EP2014 / 069696.
(Continued)

*Primary Examiner* — Lee D Wilson
(74) *Attorney, Agent, or Firm* — Seager, Tufte & Wickhem LLP (57) ABSTRACT

Apparatus (40) for compressing a transcatheter cardiac stent-valve (10) comprises: a first compressor stage (100) including a hollow channel (42) with a tapered interior surface configured for compressing a stent-valve in response to longitudinal advancement of the stent-valve within the channel; and a second compressor stage (102) comprising a crimper for compressing a portion of the stent-valve without longitudinal advancement.

13 Claims, 7 Drawing Sheets

(51) Int. Cl.
 *A61F 2/95* (2013.01)
 *A61F 2/97* (2013.01)
(52) U.S. Cl.
 CPC .............. *A61F 2002/9522* (2013.01); *A61F 2220/0008* (2013.01); *A61F 2230/0054* (2013.01); *A61F 2250/0018* (2013.01); *A61F 2250/0091* (2013.01)

(56) References Cited

U.S. PATENT DOCUMENTS

| | | |
|---|---|---|
| 6,920,674 B2 | 7/2005 | Thornton |
| 8,006,535 B2 | 8/2011 | Righini et al. |
| 8,652,145 B2 | 2/2014 | Maimon et al. |
| 8,740,839 B2 * | 6/2014 | Eaton .................. A61B 17/24 604/104 |
| 9,333,077 B2 | 5/2016 | Peter |
| 10,245,145 B2 * | 4/2019 | Mantanus ............. A61F 2/2436 |
| 2010/0121424 A1 | 5/2010 | Kubena et al. |
| 2010/0292779 A1 | 11/2010 | Straubinger et al. |
| 2016/0228249 A1 * | 8/2016 | Mantanus ............. A61F 2/2436 |

FOREIGN PATENT DOCUMENTS

| | | |
|---|---|---|
| WO | 2012023979 A2 | 2/2012 |
| WO | 2012038550 A1 | 3/2012 |
| WO | 2012116368 A2 | 8/2012 |
| WO | 2012150290 A1 | 11/2012 |
| WO | 2013177684 A1 | 12/2013 |

OTHER PUBLICATIONS

International Preliminary Report on Patentability dated Mar. 22, 2016 and corresponding to PCT / EP2014 / 069696 filed Sep. 16, 2014.

* cited by examiner

METHOD AND APPARATUS FOR COMPRESSING/LOADING STENT-VALVES

CROSS REFERENCE TO RELATED APPLICATIONS

This application claims priority to U.S. application Ser. No. 15/022,525, filed Mar. 16, 2016, which claims priority to International Patent Application No. PCT/EP2014/069696, filed Sep. 16, 2014, and entitled "Method and Apparatus for Compressing/Loading Stent-Valves," which claims priority to European Patent Application No. 13184650.3, filed Sep. 16, 2013, and entitled "Method and Apparatus for Compressing/Loading Stent-Valves." The present application incorporates herein by reference the disclosures of each of the above-referenced applications in their entireties.

TECHNICAL FIELD

The present invention relates to the field of stents for transcatheter delivery, and in particular to a method and apparatus for compressing a stent to a compressed condition and/or for loading a stent for a delivery catheter. In some non-limiting aspects, the stent is a stent-valve, for example a cardiac stent-valve. The invention has been devised while addressing problems encountered with stent-valves, but the invention may also be applicable for compressing other types of stents for transcatheter delivery.

BACKGROUND

WO-A-2012/038550 describes a cardiac stent-valve and a system for delivering the stent-valve percutaneously. The stent-valve is compressible to a compressed state suitable to be accommodated within two complementary sheaths at the delivery tip of the delivery catheter. In the compressed state, the small size enables the catheter to be introduced percutaneously, and advanced via the femoral artery, to reach the heart. The two sheaths cover different sections of the stent-valve, and are translatable in opposite directions to deploy the sections of the stent-valve in a predetermined sequence. Upon deployment, the stent-valve expands to an operative size.

The task of compressing the stent-valve on to (or ready for) the delivery catheter is complicated because the stent-valve is delicate and vulnerable to damage. Damage may result from over compression, or a nonuniform stress distribution, or buckling, or non-circularity during compression, or from tearing or abrasion of valve component tissue. A deformed or damaged stent-valve may function imperfectly, or have a reduced operational life, or may be difficult or even impossible to implant correctly. The complications are exacerbated in the case of a self-expanding type of stent-valve because a self-expanding stent-valve has a strong restoration force when compressed, and requires application of a large compression force to compress the stent-valve down to its compressed condition. Large forces are difficult to apply to a delicate stent-valve. A self-expanding stent-valve may also have more of a tendency to deform undesirably to a non-circular shape unless the shape is carefully controlled during compression. Further complications arise when the stent-valve is to be compressed for loading on to a delivery catheter having multiple sheaths that close over the stent-valve in different directions. Such sheaths limit the available room and possibilities for compressing the stent-valve.

It remains challenging to provide a technique for compressing a stent-valve, that is relatively easy and intuitive to use, inexpensive to implement, uses apparatus that is not too bulky and can conveniently be sterilized, and also avoids the problems discussed above.

SUMMARY

Reference may be made to the compressing/loading apparatus described in WO 2012/150290.

The present invention has been devised bearing the above issues in mind. It may be a non-limiting object to address and/or alleviate at least one of the above issues.

Certain aspects of the invention are defined in the claims.

Broadly speaking, a further aspect of the invention provides an apparatus for use in compressing a stent (preferably a stent-valve) for loading into a delivery catheter, the apparatus comprising a first compressor stage for compressing the stent; and a second compressor stage coupled or couplable to the first compressor stage and configured to further compress a portion of the stent after passing through the first compressor stage.

In some embodiments, the first compressor stage may comprise a hollow channel (which may optionally additionally or alternatively be referred to as a hollow channel member or hollow channel body), and the first compressor stage may be configured for progressively compressing the stent in response to, or in association with, longitudinal advancement of the stent within the hollow channel.

The second compressor stage may be configured to compress a portion of the stent at the second compressor stage without advancement of the stent within the second compressor stage, for example, when the stent is substantially stationary (e.g. at least in the longitudinal direction).

For example, with such an arrangement, the stent may be advanced in incremental steps through the apparatus. While the stent is being advanced, the first compressor stage progressively compresses the stent in response to (or in association with) advancement within the hollow channel. Once advancement of the stent is stopped, the second compressor stage can be operated to further compress a portion of the stent thereat, for example temporarily to facilitate sliding (stepwise) a constraining sheath over or towards the further compressed portion. Thereafter, the second compressor stage may be released (or relaxed), and the stent advanced a further step longitudinally, and the process repeated stepwise.

An advantage of such an arrangement is that the first compressor stage can provide controlled compression of the stent without excess loads, and the second compressor stage can provide (optionally temporary) additional local crimping at a position on the stent to facilitate sliding a relatively tightly fitting constraining sheath (e.g. of the delivery catheter) over the compressed stent.

The second compressor stage may be coupled (or couplable) to be at an exit (or exit end) of the first compressor stage.

The second compressor stage may be releasably couplable to the first compressor stage, for example, by a screw threaded coupling.

The first compressor stage may include a first manually operable actuator (e.g. first driver). Operation of the first actuator may advance the stent within the hollow channel, and compress the stent.

The second compressor stage may include a second manually operable actuator (e.g. second driver). Operation of the second actuator may further compress a portion of the stent without advancing the stent with respect to the hollow channel.

The first actuator and/or the second actuator may be rotatable. When both actuators are rotatable, they may optionally be rotatable about a common rotation axis (e.g., the longitudinal axis of the hollow channel).

Various configurations are envisaged for the first and second compressor stages, and any of the features below for each may be selected and combined as desired. All such selections are combinations are specifically envisaged herein.

For example, the second compressor stage may optionally include any one or more of the following:

(i) The second compressor stage may include a crimper unit.

(ii) The crimper may comprise one or more movable elements that define or control a variable size aperture. The crimper may be operable by driving the movable element(s) to reduce the aperture size, and bear against the stent to compress the stent.

(iii) The movable elements may be jaws. The jaws may cooperate to define a chuck mechanism.

(iv) The crimper may comprises a liner ring, defining the contact surface of the crimper for bearing against the stent. The liner ring may comprise plastics, and may be elastic or non-elastic. The term "ring" as used herein refers to any loop-like element, whether of closed or open shape.

(v) The actuator (second actuator) for operating the crimper may be or comprise a screw threaded driver. The screw threaded driver may rotate about the longitudinal axis of the apparatus.

(vi) In some embodiments, the second compressor stage may be releasably coupled (or releasably couplable) to the first compressor stage. In a preferred embodiment illustrated hereafter, a screw threaded element provides both a releasable coupling, and crimper operation as described above. Initial turning (e.g. tightening) of the screw-threaded element can mechanically couple the compressor stages together. Further turning (e.g. tightening) of the screw-threaded element operates the crimper. To release or deactivate the crimper, movement of screw-threaded element is reversed. Initial reverse movement (e.g. untightening) releases or relaxes the crimper. Further reverse movement (e.g. untightening) releases or disconnects the compressor stages from each other.

For example, the first compressor stage may optionally include any one or more of the following:

(i) the hollow channel may have an interior surface shaped for progressively compressing the stent in response to longitudinal advancement of the stent within the hollow channel.

(ii) the first compressor stage may further comprise a mover for applying a longitudinal driving force to the stent for advancing the stent within the hollow channel.

(iii) the apparatus further comprises a driver for generating a driving force, the mover being configured to transmit the driving force from the driver to the stent to advance the stent within the channel. The driver may be mounted externally of or on the channel, for example, radially externally or radially outside. The driver may comprise a member rotatable externally around the longitudinal axis of the channel, and a screw thread and/or helical guide for generating longitudinal motion in response to the rotation. For example, the driver may be threadedly coupled to the exterior of the channel. In some embodiments, the channel has (i) a generally cylindrical exterior portion carrying a screw thread for the driver, and/or (ii) a generally non-cylindrical interior portion for collapsing the stent-valve. The generally non-cylindrical interior portion may optionally comprise a substantially round cross-section shape that reduces in diameter progressively along one or more regions of the longitudinal axis.

(iv) the hollow channel may comprise at least one slot through a wall thereof, and the mover may comprise a portion slidable in the slot and projecting therethrough for engaging a stent within the channel. The slot may be substantially linear and/or longitudinally extending. Optionally the channel comprises two slots, or optionally the channel comprises three slots, or optionally the channel comprises four slots, or optionally the channel comprises five slots, or optionally the channel comprises six slots, or optionally more. The mover may comprise a corresponding number of said portions, one for each slot. Additionally or alternatively, the hollow channel may comprise a member having at least one slot extending therein. For example, the slot may extend over at least 50% of the axial length of the member, optionally at least 55%, optionally at least 60%, optionally at least 65%, optionally at least 70%, optionally at least 75%, optionally at least 80%, optionally at least 85%, optionally at least 90%, optionally at least 95%. Alternatively, the hollow channel may comprise a plurality of members assembled (or assembleable) together to define the hollow channel form collectively. In either case, the slots may optionally be open at at least one end of the channel, to permit the mover to be separated from the channel by sliding out of the open ends of the slots.

(v) Optionally, the hollow channel comprises a plurality of slots, and the mover comprises (i) a plurality of said portions slidable in slots, and (ii) a portion fitting outside, e.g. radially outside, the channel (e.g. radially outside the circumferential periphery of the channel). The portion fitting outside may interconnect, radially outside the channel, the portions slidable in the slots.

For example, the portion fitting outside may connect radially-outer ends of the portions slidable in the slots.

(vi) The mover may be configured to apply the longitudinal driving force to at least one (optionally two, or optionally three, or optionally four, or optionally more) circumferential positions around the circumference of the stent. This may enable the driving force to be applied to one or more specific circumferential positions at which the stent (e.g. stent-valve) is relatively robust and/or is less vulnerable to damage or deformation. For example, the one or more circumferential positions to which the force may be applied may be substantially aligned with commissural supports or posts of a stent-valve. Alternatively, the one or more circumferential positions to which the force may be applied may be substantially non-aligned with commissural supports or posts of a stent-valve.

(vii) The mover may be configured to apply the longitudinal driving force to at least one (optionally two, or optionally three, or optionally four, or optionally more) longitudinal positions along the axial length of the stent. This may enable the driving force to be applied to one or more specific longitudinal positions at which the stent is relatively robust and/or is less vulnerable to damage or deformation. For example, the one or more longitudinal positions to which the force may be applied may correspond to commissural supports or posts of a stent valve. Additionally of alternatively, each of the one or more longitudinal positions may correspond to a valley in the stent profile or structure (for example a valley defined at a junction of apex between two struts).

(viii) The mover may be configured to apply the longitudinal driving force to at least one (optionally two, or optionally three, or optionally four, or optionally more) specific positions that are intermediate the extreme ends of the stent. This may enable a "pushing" force to be applied with less risk of buckling the stent axially. Additionally or alternatively, it may enable a "pulling" force to be applied without relying on or interfering with the extreme ends of the stent. The stent may comprise one or more attachment elements at an extreme end of the stent. Such an arrangement does not interfere with or complicate the engagement by the attachment elements. Additionally of alternatively, each of the positions may correspond to a valley or concavity in the stent profile or structure (for example a valley defined at a junction of apex between two struts). Optionally, the at least one position may be: spaced from both opposite ends of the stent by at least 5 mm, preferably at least 10 mm; and/or spaced from both opposite ends of the stent by at least 10% of a maximum length of the stent-valve, preferably at least 15%.

(ix) The mover may comprise a ring extending around the exterior of the channel, and one or more limbs extending or projecting inwardly from the ring. The limbs may be blade-like and/or finger-like and/or pin-like and/or spokelike. The ring may be slidable longitudinally around the exterior of the channel. Each limb may extend through a respective slot in the channel wall to extend towards the interior of the channel. Each limb may be slidable in the respective slot. The inner ends of the limbs may be substantially free, or the inner ends may be coupled to each other, for example, either meeting at a common point (e.g. centre) or coupled via an inner ring.

(x) The portion or a surface of the mover configured for engagement with the stent (e.g. each limb described above, if used) may extend in a generally radial direction with respect to the channel axis and/or the plane of the ring (if used). Alternatively, the portion or a surface of the mover configured for engagement with the stent may be inclined with respect to the radial direction and/or ring plane. In one form, the portion is inclined in a direction towards an exit and/or narrower (e.g. internally narrower) end of the channel. The angle of inclination (e.g. towards the exit/narrow end) may be about 5° (or more), about 10° (or more), about 15° (or more), or about 20° (or more). The angle of inclination may be between about any two of above values, for example, between about 5° and about 15°. The inclination may reduce the risk of the stent buckling under axial compression loads. The inclination may tend to urge modestly the stent in a radial outward direction instead of radially inwardly. Modest radial outward urging is countered by contact with the interior surface of the channel, thereby enabling the shape of the stent to be controlled to avoid buckling.

(xi) The interior surface of the hollow channel may be substantially fixed and/or immovable, at least in a radial direction. The compression of the stent-valve may be achieved at least predominantly (and preferably entirely) as a result of longitudinal displacement of the stent-valve within the channel, without substantial radial movement of the interior surface of the channel.

(xii) The interior surface of the hollow channel may comprise at least one non-cylindrical portion, for example, having a diameter that reduces progressively along the longitudinal axis of the channel in a direction towards an exit. Additionally or alternatively, the channel may comprise at least one generally cylindrical portion. In the illustrated embodiments, the interior surface comprises at least two non-cylindrical portions. The portion of the interior surface adjacent to the entrance to the channel may be generally cylindrical. The portion of the interior surface adjacent to the exit of the channel may be generally non-cylindrical.

(xiii) The longitudinal length of the hollow channel may be longer than the stent-valve such that, in use, the stent-valve is contained entirely within the channel when being advanced.

(xiv) In use, the stent-valve may be passed entirely through the hollow channel from an entrance at one end to an exit at the opposite end.

(xv) The stent-valve may be advanced inflow-end first within the hollow channel. The inflow-end may be a first end to emerge from an exit of the hollow channel. Alternatively, the stent-valve may be advanced outflow-end first within the hollow channel. The outflow-end may be a first end to emerge from an exit of the hollow channel.

Whether or not the above features are used, the apparatus may optionally further comprise at least one loading tube (which may optionally additionally or alternatively be referred to as a channel extension or an exit extension) for or usable at the exit and/or narrow (e.g. internally narrower) end of the first and/or second compressor stage. The loading tube may be removably attachable to the channel, or it may be associated with the channel by holding in place by hand, or it may be insertable into the exit of the channel. When the extension is separated (e.g. removed) from the channel, this may permit the end of the stent to be observed at the exit/narrow end of the channel for loading onto, or engagement with, a delivery catheter. After loading/engagement of the stent end to a delivery catheter, the extension may be placed, inserted or re-placed (e.g. attached or reattached) with respect to the channel. In some embodiments, the loading tube has a bore therein. In some embodiments, the bore may have substantially the same diameter as the exit end of the channel. In other embodiments, the bore and/or the outer diameter of the loading tube may be slightly smaller than the diameter at the exit of the channel.

In some embodiments, the loading tube may be attachable by a fixing that withstands longitudinal load between the channel and the extension. For example, the fixing may be a screw threaded fixing. In other embodiments, the loading tube may be insertable at least partly into the channel at or through the exit.

In a further aspect, the invention provides loading tube apparatus for use in compressing and/or loading a stent (preferably a stent-valve) for a delivery catheter, the loading tube apparatus comprising:

a plurality of segments that are assemblage around a portion of a delivery catheter to define a tubular shape; and
at least one retainer for retaining the plurality of segments in the assembled shape.

Such an apparatus can enable a loading tube to be fitted on to a delivery catheter, the loading tube having a smaller inner diameter than can or could otherwise easily be slid onto the delivery catheter. Instead, the plurality of segments may be placed and assembled at the desired position on the delivery catheter to define a tubular shape, and secured in the assembled shape by the retainer.

In some embodiments, the retainer may comprise at least one threaded nut, and/or a supporting overtube. The nut and/or overtube may have an inner diameter sufficiently large to be slid on to the delivery catheter.

The loading tube apparatus as aforesaid may optionally be used in combination with the previously described (multi-compressor stage) compressing apparatus. The two may be especially useful when loading a stent on to a multiple-sheath delivery system in which the multiple sheaths close over respective portions of the stent from opposite first and second directions. For example, the compressor apparatus may be suitable for compressing/loading a first portion of the stent into a first of the sheaths. The loading tube apparatus may be suitable for loading a second portion of the stent into a second of the sheaths. The two apparatus may be used one after the other, or both at the same time.

In a further aspect, the invention provides a method of loading a stent (preferably a stent-valve) on to a delivery catheter, the method comprising: (a) operating a first compressor stage of a compressing apparatus, to advance the stent within a hollow channel of the first compressor stage, and compress the stent in response to, or in association with, the advancement within the hollow channel;

(b) operating a second compressor stage of the compressing apparatus to further compress a portion of the stent without advancing the stent further;

(c) sliding a constraining sheath of the delivery apparatus over an exposed portion of the stent valve that has advanced through the first and second compressor stages.

(d) repeating steps (a), (b), (c) in sequence one or more times to progressively compress and load at least a portion of the stent on to the delivery catheter.

In a further aspect, the invention provides a method of loading a stent (preferably a stent-valve) on to a multiple-sheath delivery catheter, the catheter having first and second sheaths that close over respective portions of the stent-valve from opposite directions, the method comprising:

(a) providing a compressor apparatus having at least a first compressor stage with a hollow channel (which may optionally additionally or alternatively be referred to as a hollow channel member or hollow channel body) and configured for progressively compressing the stent in response to or in association with longitudinal advancement of the stent within the hollow channel; and (b) advancing and compressing at least a portion of the stent-valve using the compressor apparatus;

(c) closing a first sheath over an exposed compressed portion of the stent compressed by the compressor apparatus;

(d) optionally repeating steps (a), (b) and (c) one or more times;

(e) providing a loading tube apparatus around a portion of the delivery catheter by assembling a plurality of segments to define a tubular shape and retaining the segments together with a retainer.

(f) closing the second sheath over a second portion of the stent, using the loading tube at a mouth of the second sheath, to facilitate entry of the second portion of the stent into the sheath.

In some embodiments, the compressor apparatus may further comprise a second compressor stage, and the method may further comprise between steps (b) and (c) a further step of operating the second compressor stage without advancing the stent, to further compress locally a portion of the stent-valve to facilitate closing the first sheath in step (c). This additional step may be repeated in sequence as part of step (d).

In some embodiments, the method may further comprise a step of sliding an intermediate loading tube over the stent at least between steps (d) and (f) to facilitate the method.

In a further aspect, the invention provides apparatus for compressing a transcatheter cardiac stent-valve comprising: a first compressor stage including a hollow channel with a tapered interior surface configured for compressing a stent-valve in response to longitudinal advancement of the stent-valve within the channel; and a second compressor stage comprising a crimper for compressing a portion of the stent-valve without longitudinal advancement.

Features and advantages of the invention in its various aspects include one or more of: (i) relatively easy and intuitive to use (ii) inexpensive to implement, (iii) uses apparatus that can conveniently be sterilized, (iv) avoids interfering with an attachment region at one end of the stent, (v) avoids buckling of the stent, (vi) provides accurate control of the stent shape during compression, (vii) facilitates loading of the stent on to a multi-sheath delivery catheter, (viii) enables compression of at least a significant portion of the stent to be achieved without stressing engagement with a stent holder of the delivery catheter, and/or (ix) can easily be performed by a single operator.

Although various features and ideas of the invention are described above and defined in the appended claims, additional features and advantages will become apparent from the following non-limiting description of detailed embodiments. Protection is claimed for any novel feature or idea described herein and/or illustrated in the drawings whether or not emphasis has been placed thereon.

BRIEF DESCRIPTION OF DRAWINGS

Non-limiting embodiments of the invention are now described by way of example only, with reference to the accompanying drawings, in which:—

Before describing the compression apparatus in detail, an example stent (stent-valve) is first described so that the features and functions of the compression apparatus may fully be appreciated.

DETAILED DESCRIPTION

Figure 1:
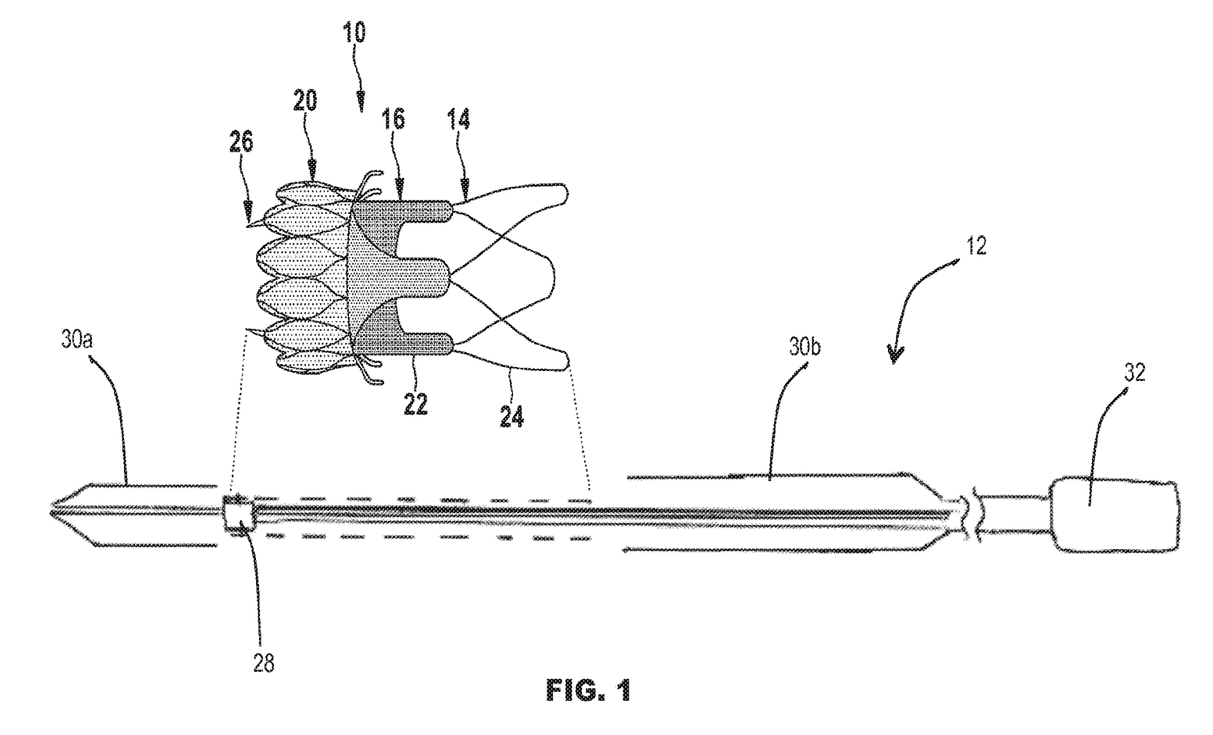
FIG. 1 is a view of a stent-valve and delivery catheter.
Figure 2:
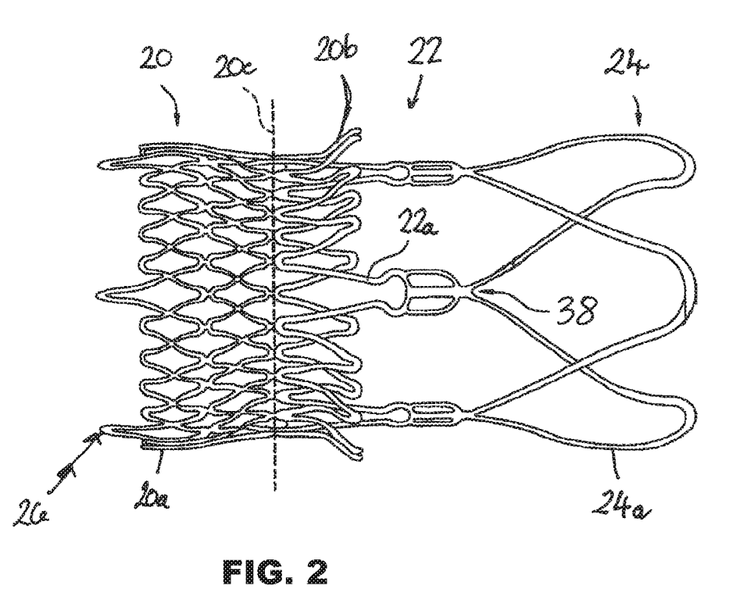
FIG. 2 is a schematic side view of the stent component of the stent-valve of FIG. 1.

FIGS. 1 and 2 illustrate an example stent in the form of a stent-valve 10. The stent-valve 10 may be a cardiac stent-valve, for example an aortic stent-valve. The stent-valve 10 may be configured for transcatheter implantation in the body, for example enabling the use of minimally invasive techniques. The stent-valve 10 may be configured for transcatheter aortic valve implantation ("TAVI"). Although a particular geometry of stent-valve 10 is illustrated by way of example, it will be appreciated that the invention is not limited to any specific stent-valve geometry. The example geometry is used herein because it enables advantages of the invention to be emphasized.

The stent-valve 10 may be transformable between an expanded state (as illustrated in FIG. 1), and a compressed state indicated by the broken line 10'. The expanded state may correspond approximately to an operative state of the stent-valve after implantation. The stent-valve 10 may not fully achieve the expanded state at implantation, tolerance being allowed for size mismatching and/or for slight compression to maintain an outward resilient bias for a friction fit in the native anatomy. The compressed state 10' may correspond to a delivery state to be accommodated by a delivery catheter 12 and/or for introduction into the anatomy to the desired implantation site.

The stent-valve 10 may be of a self-expanding type that is resiliently biased towards the expanded state, and is compressible to the compressed state 10' by application of suitable radial compression forces. The stent-valve 10 remains in its compressed state while constrained. When the constraint is removed, the stent-valve 10 self expands towards the expanded state. Alternatively, the stent-valve 10 may be of a non-self-expanding type that requires application of an expansion force to transform the stent-valve 10 from the compressed state 10' to the expanded state.

The stent-valve 10 may comprise a stent component 14 and a valve component 16. The stent component 14 may provide an anchoring function for anchoring the stent-valve in the native anatomy and/or a support function for supporting the valve component 16. The stent component 14 may be of any suitable material or materials. The stent component 14 may be of metal.

Example materials include shape memory and/or superelastic alloys (for example, nitinol), stainless steel, or cobalt-chromium alloy. In the illustrated form, the stent component 14 is self-expanding and is of shape memory/superelastic alloy (e.g. nitinol). However, the stent component 14 could also be substantially non-self-expanding.

The stent component 14 may have any profile desired for anchoring and/or aligning the stent-valve 10 with respect to the native anatomy at the desired implantation site. In some embodiments, the stent component 14 may be generally cylindrical in shape, or comprise one more generally cylindrical portions or portions lying on a generally cylindrical surface (e.g. 20c and 22a). Additionally or alternatively, the stent component 14 may be generally non-cylindrical in shape or comprise one or more generally non-cylindrical portions or portions lying on a non-cylindrical surface (e.g. 20a, 20b, and 24). Additionally or alternatively, the stent component 14 may comprise one or more anchor projections, and/or one or more stabilization portions.

In the illustrated from, the stent component 14 optionally comprises an anchoring portion 20 defined, for example, by an inferior crown 20a and a superior crown 20b that define a groove and/or waist 20c therebetween. The anchoring portion 20 may have a first resistance to compression, and may comprise a cellular lattice.

The stent component 14 optionally (further) comprises a valve support portion 22 comprising, for example, a plurality (e.g. three) commissural support posts 22a. The commissural support posts 22a may be arranged on a pitch circle diameter smaller than an extremity of at least one of the crowns 20a and 20b. The commissural support posts 22a may be arranged on a pitch circle diameter corresponding to the waist 20c. The commissural support posts 22a may partly overlap at least one of the crowns 20 and 22 in the axial direction, and extend axially beyond that respective crown. The commissural support posts 22a may be frame-like. The commissural support posts 22a may have a shape that follows, at least approximately, a peripheral contour of the valve, at least in the region of the valve periphery adjacent to the commissural support posts.

The stent component 14 optionally (further) comprises a stabilization or alignment portion 24 defined, for example, by a plurality (e.g. three) wings or arches 24a. The arches 24a may extend from tips of the commissural support posts 22a, to define a vaulted structure thereover. The alignment portion 24 may have a greater flexibility than the anchoring portion 20 and/or the valve support function 22. The alignment portion 24 may have a second resistance to compression that is smaller than the first resistance to compression of the anchoring portion 20. The alignment portion 24 may be less rigid (e.g. radially) than the anchoring portion 20 and/or the valve support portion 22.

The stent component 14 optionally (further) comprises an attachment portion 26 for attaching the stent component 14 to a stent receiver 28 of the delivery catheter 12. In the illustrated embodiment, the stent receiver 28 may be a stent holder and will be referred to as such hereinafter, although other types of receiver for receiving and/or accommodating at least a portion of the stent-valve 10 may be used as desired. The attachment portion 26 may comprise one or more geometrical openings, or one or more lugs or other projections, for forming an interference (e.g. interlocking) fit with a complementary portion of the stent holder 28. The attachment portion 26 may be arranged at or adjacent to at least one extreme end of the stent component 14. In the present embodiment, the attachment portion 26 is defined by a plurality (e.g. three) of extensions of cells of the inferior crown 20a.

The valve component 16 may be of any suitable natural and/or synthetic material(s). For example, the valve component 16 may comprise porcine and/or bovine pericardium and/or harvested natural valve material. The valve component 16 may comprise a plurality of leaflets arranged to coapt or collapse to a closed position to obstruct flow in one direction therepast, while flexing apart to an open position to allow flow in an opposite direction. The valve component 16 may be accommodated at the valve support portion 22 and/or at least partly within the anchoring portion 20. The stent-valve 10 (e.g. the valve component 16) may further comprise an inner skirt and/or an outer skirt covering at least partly a respective inner or outer surface portion of the stent component 14. For example, the skirt(s) may cover at least a portion of the anchoring portion 20 and/or at least a portion of the valve support portion 22.

Still referring to FIG. 1, the delivery catheter 12 may by way of example only, comprise multiple sheaths 30 at a containment region of the delivery catheter 12, for accommodating a stent-valve 10. In the present example, the sheaths 30 include a first (e.g. distal) sheath 30a and a second (e.g. proximal) sheath 30b. The sheaths 30 may be configured for covering respective portions of the stent-valve 10 in its compressed state 10', for constraining the stent-valve 10 against expansion. For example, the first sheath 30a may cover the attachment portion 26 and/or the inferior crown 20a, and the second sheath 30b may cover one or more (or all) of the superior crown 20b, the valve support portion 22, and the alignment portion 24. Each sheath 30 is translatable along the axis of the catheter to selectively cover or expose the respective region of the stent-valve 10, in response to actuation by a control at a handle end 32 of the delivery catheter 12. The first and second sheaths may translate in respective first and second opposite directions. The first and second sheaths may translate in respective opposite directions to expose the stent-valve and/or to close over the respective regions of the stent-valve. For example, the first (distal) sheath 30a may translate distally to expose the respective regions of the stent-valve previously covered by the first sheath 30a. The first (distal) sheath 30a may translate proximally for closing over these regions during loading. For example, the second (proximal) sheath 30b may translate proximally to expose the respective regions of the stent-valve previously covered by the second sheath 30b. The second (proximal) sheath 30b may translate distally for closing over these regions during loading. The stent holder 28 may prevent, or at least reduce, any tendency of the stent-valve 10 to displace axially during translation of the sheaths 30, and/or prevent, or at least reduce, any tendency of the stent-valve 10 to jump free of a respective sheath 30 when only a small portion of the stent-valve 10 is covered by the sheath 30. The stent holder 28 may be carried on a central tube 36 (or an assembly of plural tubes), for example, for receiving a guide-wire. Further detail of the delivery catheter 12 may be found in the aforementioned WO-A-2012/038550, the entire content of which is incorporated herein as if reproduced in full in the present description. Other designs of delivery catheter 12 may be used, for example, without a sheath 30 and/or without a stent holder 28. The example delivery catheter 12 is used herein because it enables advantages of the invention to be emphasized.

The maximum outer diameter of the stent-valve 10 in its expanded state may be from about 25 mm to about 35 mm. In contrast, the maximum outer diameter of the stent-valve in its compressed condition 10' for the delivery catheter may be significantly smaller, for example about 10 mm or less, or about 6 mm or less, or about 5 mm or less. The radial force required to be applied to compress the stent-valve may be considerable, for example, at least 50 N, or at least 75 N, or at least 100 N. In some embodiments, the radial force is between about 100 N and 120 N.

Figure 3:
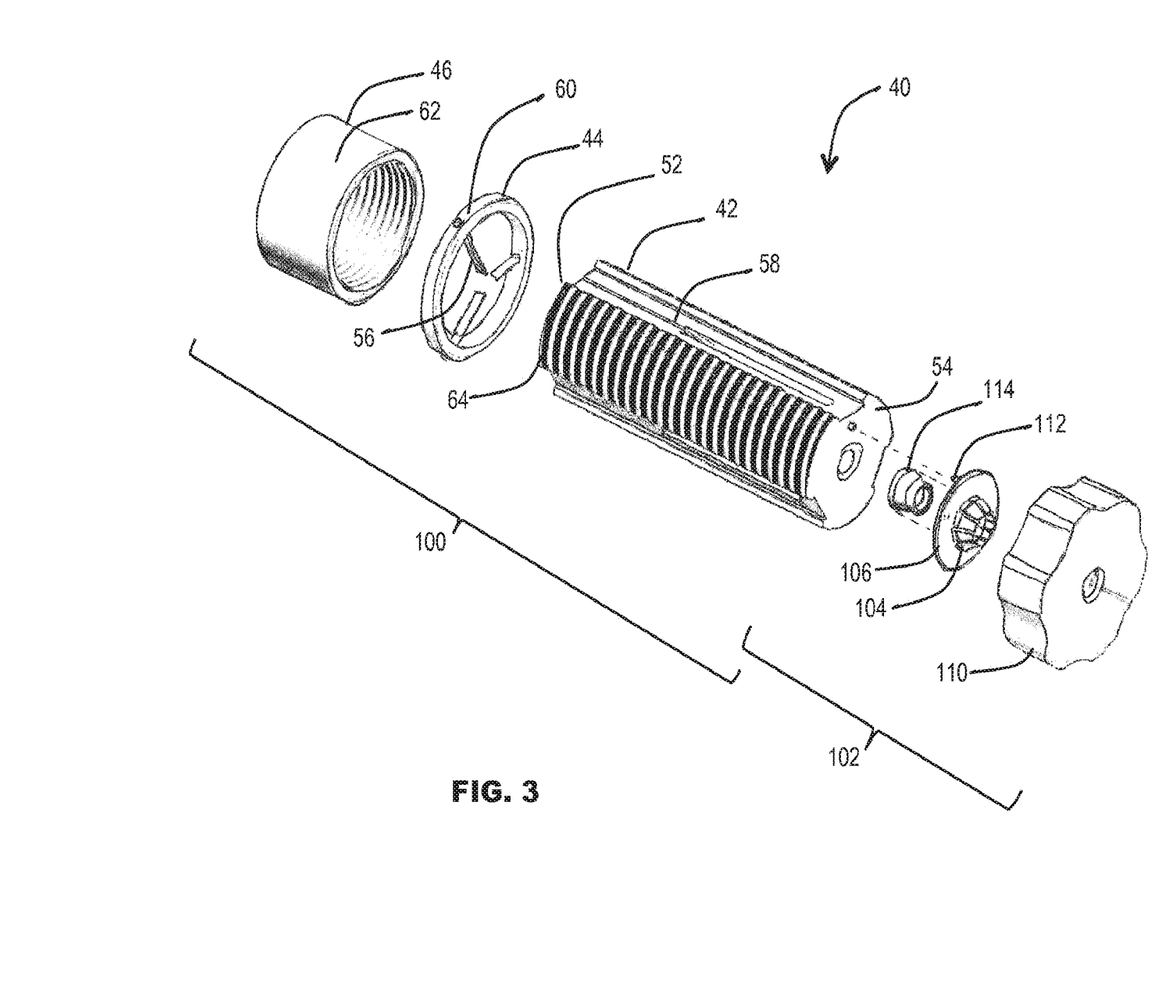
FIG. 3 is a schematic perspective exploded view of a compressor apparatus for compressing the stent valve for loading on to the delivery catheter.
Figure 4:
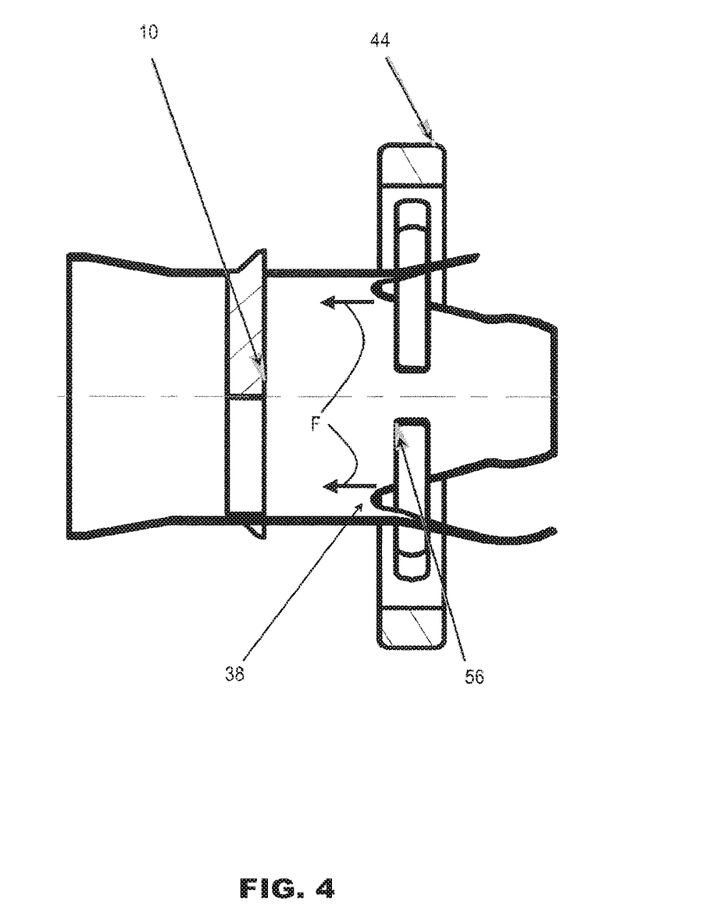
FIG. 4 is a partial schematic side view of the stent and pusher, in isolation, showing how the pusher engages the stent.
Figure 5:
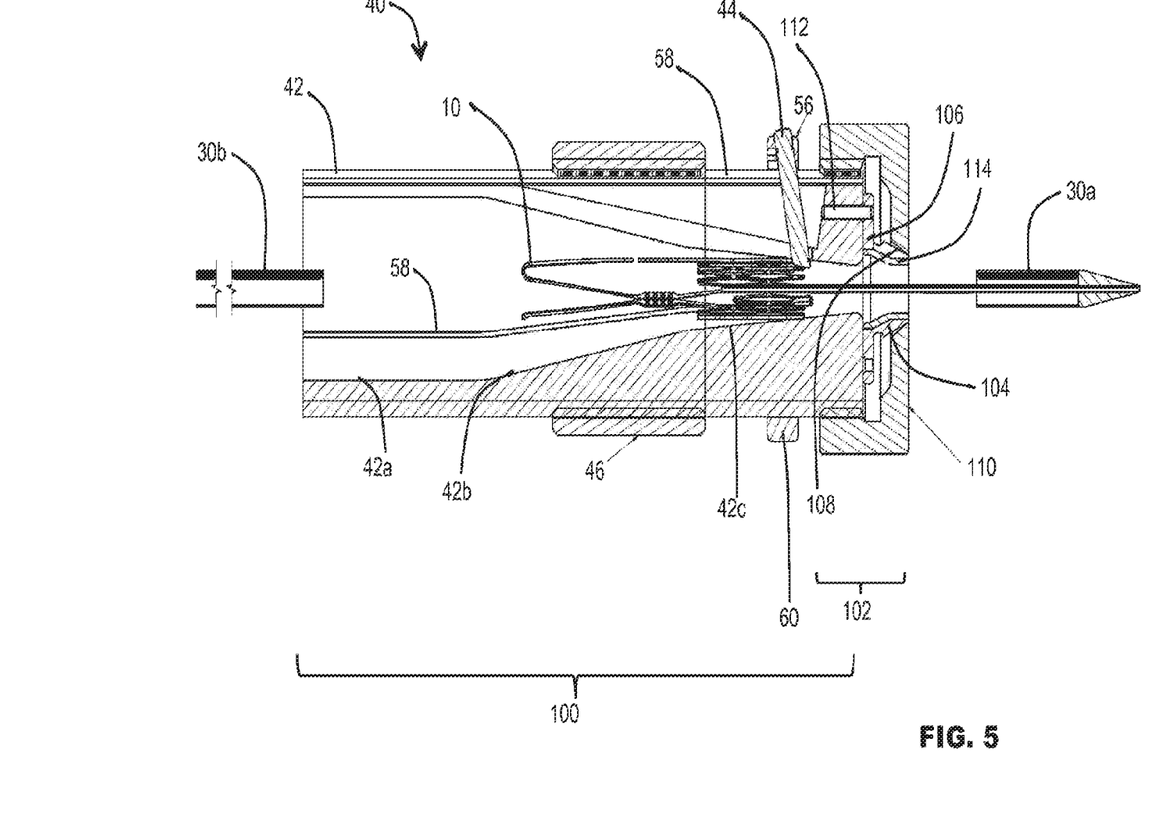
FIG. 5 is a schematic section of the compressor apparatus of FIG. 3, in use (the stent being shown within the compressor apparatus to illustrate the size, but is displaced to the left (compared to the pusher) to avoid cluttering the view of the crimper)

Referring to FIGS. 3-5, apparatus 40 is illustrated for compressing the stent valve 10 to its compressed state 10'. The apparatus 40 is also configured to facilitate loading of the stent-valve 10 on to the delivering catheter 12 as part of the compression process.

The apparatus 40 may comprise a first compressor stage 100 and/or a second compressor stage 102. When both are implemented, the second stage 102 may be coupled or couplable to further compress a portion of the stent valve 10 after passing through the first compressor stage 100. For example, the second compressor stage 102 may be coupled or couplable at, or to be at, an exit (or exit end) of the first compressor stage 100.

The first compressor stage 100 may comprise a hollow channel (or hollow channel member or hollow channel body) 42, and the first compressor stage 100 may be configured for progressively compressing the stent valve 10 in response to, or in association with, longitudinal advancement of the stent valve 10 within the hollow channel 42.

The second compressor stage 102 may be configured to compress a portion of the stent at the second compressor stage without advancement of the stent within the second compressor stage, for example, when the stent is substantially stationary (e.g. at least in the longitudinal direction).

As will be described later, with such an arrangement, the stent may be advanced in incremental steps through the apparatus. While the stent is being advanced, the first compressor stage 100 progressively compresses the stent in response to (or in association with) advancement within the hollow channel. Once advancement of the stent is stopped, the second compressor stage 102 can be operated to further compress or pinch a portion of the stent thereat, for example temporarily to facilitate sliding (stepwise) a constraining sheath over or towards the further compressed portion. Thereafter, the second compressor stage 102 may be released (or relaxed), and the stent advanced a further step longitudinally, and the process repeated stepwise.

An advantage of such an arrangement is that the first compressor stage 100 can provide controlled compression of the stent without excess loads, and the second compressor stage 102 can provide (optionally temporary) additional local crimping or pinching at a position on the stent to facilitate sliding a relatively tightly fitting constraining sheath (e.g. of the delivery catheter) over the compressed stent.

The first compressor stage 100 will now be described in more detail. In addition to the channel 42, the first compressor stage 100 may further comprise a mover 44 and a driver 46. Some or all of the components 42-46 may be disassemblable from each other, and assembled (captively or non-captively) during use of the apparatus 40.

The hollow channel 42 may have an interior surface 50 shaped for progressively compressing the stent-valve 10 in response to longitudinal advancement of the stent-valve 10 within the channel 42 from an entrance 52 at one end to an exit 54 at the opposite end. The interior surface 50 may be generally round in cross-section, in order to maintain the round shape of the stent-valve 10 during compression. The interior surface 50 may comprise one or more non-cylindrical portions 50b and 50d, for example, having a diameter that reduces progressively (e.g. converges) along the longitudinal axis of the channel 42 in a direction towards the exit 54. Such a shape may be referred to as a funnel shape. The funnel may be straight sided or concave or convex in profile. The interior surface 50 may further comprise one or more generally cylindrical portions 50a. The interior surface 50 may be coated to reduce the friction between the surface 50 and the stent-valve 10 e.g. with a hydrophobic silicone based coating.

In the illustrated embodiment, a generally cylindrical portion 50a is provided adjacent to the entrance 52 of the channel 42. The cylindrical portion 50a may facilitate initial insertion of the stent-valve 10 into the channel 42 without substantial compression (and in the case of a self-expanding stent-valve, without any tendency for the stent-valve to spring back out of the entrance 52). Additionally or alternatively, a generally non-cylindrical portion 50d (e.g. funnel shaped) may be provided adjacent to the exit 54 of the channel 42. The non-cylindrical portion 50d may promote a convergent (e.g. conically tapered) shape at the end of the stent-valve 10 when emerging at the exit 54, to facilitate engagement of the stent-valve 10 with the stent holder 28 of the delivery catheter 12 during loading.

The wall(s) of the channel 42 may be generally stationary or fixed, at least in a radial direction. Compression of the stent-valve 10 is achieved by advancing the stent-valve 10 within the channel 42, such that the stent-valve 10 bears against the interior surface 50 and is forced to compress in order to advance therealong and/or therepast.

The mover 44 may be configured for applying a longitudinal driving force generated outside the channel 42, to the stent-valve 10 within the channel 42, in order to advance the stent-valve 10 within the channel 42. The mover 44 may be configured for applying the longitudinal driving force from radially outside the channel 42, to the stent-valve 10, in order to advance the stent-valve 10 within the channel 42. The mover 44 may comprise one or more portions (e.g. limbs) 56 that slide in respective slots 58 in the wall of the channel 42, and project from outside the channel 42 through the slots 58 into the interior of the channel 42. The (limb) portions 56 are configured for engaging portions of the stent-valve 10 to advance the stent-valve 10 as the mover 44 is driven to translate longitudinally.

Applying the driving force using such a mover 44 may enable the driving force to be applied to the stent-valve at one or more positions that are intermediate the opposite ends of the stent. This may enable a "pushing" force to be applied with less risk of buckling the portion of the stent under axial compression load. Additionally or alternatively, it may allow a force ("pulling" or "pushing") to be applied without interfering with the extreme ends of the stent, nor relying on or using the attachment portion 26.

Alternatively, the mover 44 may enable the driving force to be applied at an extreme end of the stent-valve 10, yet solve the problem of how to advance a stent-valve (i) through a hollow channel that is longer than the stent-valve and/or (ii) applying a pushing force to a portion of the stent-valve that itself becomes compressed.

Additionally of alternatively, applying the driving force using such a mover 44 may enable the driving force to be applied at one or more positions (radial and/or longitudinal) at which the stent is relatively robust and/or is less vulnerable to damage or deformation.

In the present example, the driving force is intended to be applied to the commissural support posts 22a (see FIGS. 2 and 4). The driving force "F" may be applied at the junctions between the commissural support posts 22a and the alignment arches 24a connected to each respective post 22a. The driving force may be applied in the hollow 38 (also referred to as a valley or concavity) between two adjacent arches 24a. Using such a technique, the mover 44 can contact the stent-valve 10 at a position that is (i) clear of the valve component and the skirt(s), in order to avoid damage thereto, and/or (ii) clear of the lattice structure of the anchor portion 20 that is densely packed during compression. The commissural support posts 22a may provide robust support for receiving the driving force, stronger than for example the stabilization portion 24.

The (limb) portions 56 may have any suitable shape and configuration desired for engaging the stent-valve 10. In the illustrated form, each limb portion 56 is generally rectangular and/or generally planar in cross-section shape. The limb portion 56 may have a blade form. The cross-section shape may provide a relatively thin and/or flat surface contacting the stent-valve 10. The cross-section shape may define a first dimension contacting the stent-valve 10 that is smaller than a dimension of the shape that is generally transverse to the first dimension.

Such a shape or shapes may reduce any tendency for the limb portion 56 to wedge open a space in the stent-valve 10, while still providing the limb portion 56 with adequate bending strength to transmit the driving force cantileverwise to the stent-valve 10 through the slots 58.

In some embodiments, the limbs 56 may extend inwardly in a generally radial direction (e.g. perpendicular to the longitudinal axis of the channel 42). Alternatively, in the form illustrated, each limb portion 56 may be inclined relative to the radial direction. The angle of inclination may be about 5° or more, optionally about 10° or more, optionally about 15° or more or optionally about 20° or more. Additionally or alternatively, the angle of inclination may be not more than about 30°, optionally not more than about 25°, optionally not more than about 20°, optionally not more than about 15°, optionally not more than about 10°. The limb portions 56 may be inclined in a direction towards the exit 54 of the channel 42 when the mover 44 is mounted thereon (such that the inner tips of the limb portions 56 incline towards the exit 54, as indicated by arrow 56a in FIG. 4). Such an arrangement may prevent, or at least reduce, any tendency for the stent-valve to buckle inwardly during compression. Instead, the inclination biases the stent-valve modestly outwardly towards the surface 50, the presence of the surface 50 obstructing outward buckling. In other embodiments, a different angle of inclination and/or a different direction of inclination may be used. In yet other embodiments, the limbs 56 may extend inwardly in a substantially radial direction.

In the illustrated form, the radially inner tips or ends of the limb portions 56 are free and define a clearance (e.g. central clearance) therebetween. The clearance enables a portion of the delivery catheter 12 to be accommodated as the stent-valve 10 is loaded on to the delivery catheter 12 as part of the compression process. The clearance may be sufficiently large to enable the radially inner tips to pass over the sheaths 30 of the catheter while the mover remains assembled to the hollow channel (e.g. in coaxial alignment). This can facilitate removal of the apparatus 40 from the catheter after loading. In other forms, the clearance may be smaller than the sheaths 30, in which case it may be appropriate to disassemble the mover from the hollow channel in order to allow the mover to pass over the sheaths 30 (e.g. moved out of coaxial alignment).

The mover 44 may optionally further comprise a ring 60 that carries the limb portions 56, and/or from which the limb portions 56 extend. The ring 60 may fit around the outside of the channel 42, and be slidable longitudinally along at least a portion of the length of the channel (e.g. slidable along at least a portion corresponding to the extent of the slots 58). The slots 58 may be open at at least one end of the channel 42 (e.g. the entrance 52) to enable the mover to be disengaged from the channel 42 for introducing a stent-valve 10 at the entrance.

The channel 42 may be made substantially as a single member having the slots 58 formed therein (as illustrated in the preferred embodiment). Alternatively, the channel 42 may comprise a plurality of component parts that are assemblage together to define collectively the channel form.

In some embodiments, the mover 44 may be driven directly by hand, but in the preferred embodiments, the driver 46 may provide additional convenience and control for generating and applying (e.g. homogenously) a driving force for the mover 44.

The driver 46 may be movable with respect to the channel 42 and be coupled (or couplable) to the channel 42 for generating the driving force in response to relative movement applied to the driver 46. The driver 46 may be external to the channel 42. For example, the driver 46 may comprise a rotary member 62 rotated by hand or by using a suitable tool. The rotary member 62 may be rotatable around the longitudinal axis of the channel 42. The rotary member 62 may be coupled (or couplable) to the channel 42 by means of a screw thread 64 and/or a helical guide, in order to generate longitudinal displacement in response to rotation of the rotary member 62. The driver 46 (e.g. the rotary member) bears directly or indirectly against the mover 44 (e.g. against the ring), to apply the driving force thereto as the rotary member 62 is rotated. The (limb) portions 56 transmit the driving force to the stent-valve 10 to advance the stent-valve 10 within the channel 42.

In the illustrated form, the channel 42 has a generally cylindrical exterior portion carrying the screw thread 64 for the rotary member 62. The rotary member 62 may be unscrewed and disassembled from the thread 64, for example, at the entrance 52 of the channel 42. Such unscrewing/disassembly permits removal of the mover 44 for insertion of the stent-valve into the entrance 52 of the channel 42, and subsequent refitting of the mover 44 and the rotary member 62.

The second compressor stage 102 may be releasably coupled or couplable at, or to be at, the exit 54 of the channel 42. The second compressor stage 102 may comprise a crimper for crimping, or pinching, a portion of the stent valve 10 within the second compressor stage 102.

In the illustrated form, the crimper comprises a plurality of movable elements in the form of chuck jaws 104. The chuck jaws 104 may be separate from each other, but in the preferred embodiment, the chuck jaws 104 are integral with a supporting base or washer 106. For example, the washer 106 and jaws 104 are provided by a one-piece plastics molding. The chuck jaws 104 are biased naturally to an outward or relaxed position, and are displaceable inwardly by contact with a conical ramp surface 108 of a surrounding actuator or driver 110. The actuator 110 is threadedly movable with respect to the channel 42, such that rotation of the actuator 110 results in its axial movement, causing the conical ramp surface 108 to bear against the chuck jaws 104 forcing them inwards. The chuck jaws 104 control the size of an aperture of the crimper. The base 106 may restrained against rotation (from frictional engagement by the actuator 110) by means of a keyed connection 112 between the base 106 and the channel 42. The keyed connection may be formed, for example, by at least one axial pin or other projection of one component fitting in an aperture of the other component.

A liner 114 fitting inside the chuck jaws 104 may provide a contact surface of the crimper for bearing against the stent-valve 10. The liner 114 may have a generally ring shape, either of closed-loop or open-loop (or split) configuration. The liner 114 may be of plastics (for example, elastic or non-elastic). In one form, the liner is of polyether block amide (PEBA).

The second compressor stage 102 may be releasably attachable to the first compressor stage 100 by a screw threaded connection. In the illustrated form, the actuator 110 provides both a releasable screw threaded connection to the channel 42, and crimper operation as described above. Initial turning (e.g. tightening) of the screw-threaded actuator 110 can mechanically couple the compressor stages together. Further turning (e.g. tightening) of the actuator 110 operates the crimper. To release or deactivate the crimper, movement of actuator 110 is reversed. Initial reverse movement (e.g. untightening) releases or relaxes the crimper. Further reverse movement (e.g. untightening) releases or disconnects the compressor stages from each other.

Figure 6:
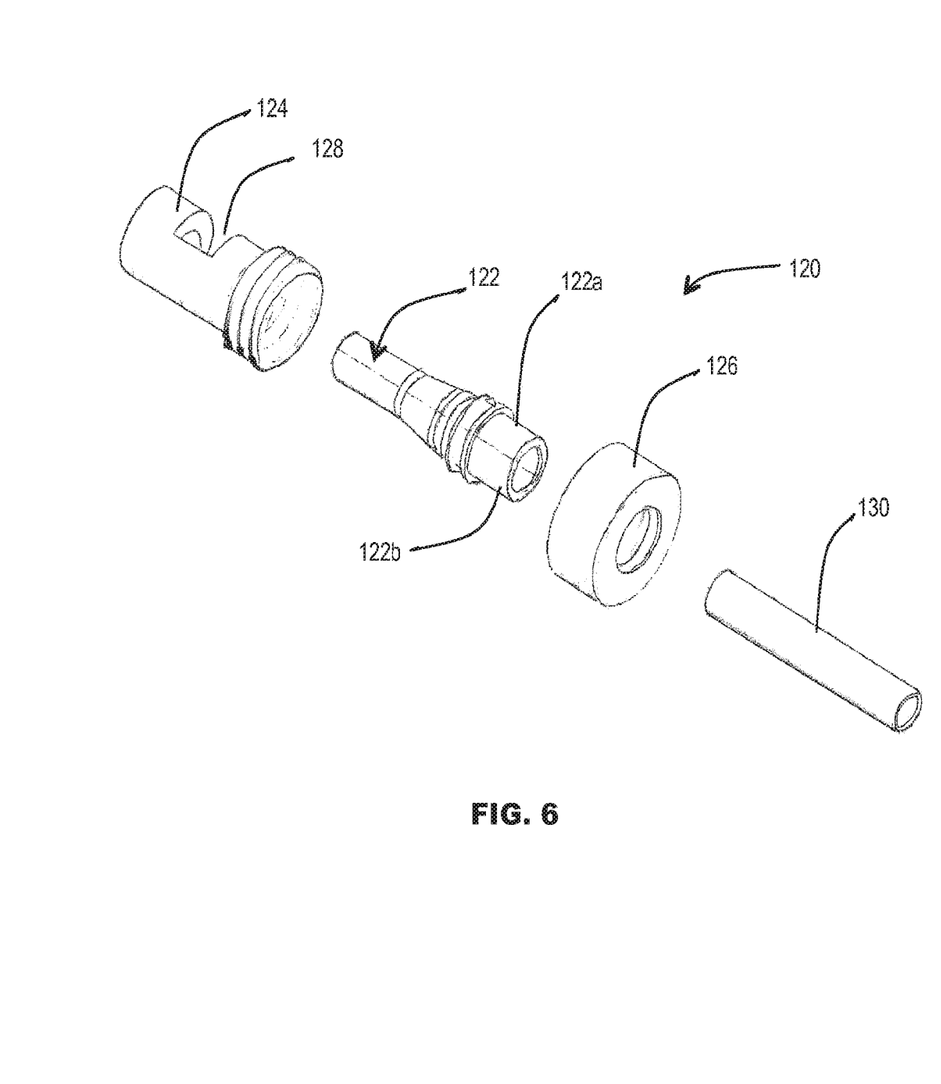
FIG. 6 is a schematic perspective exploded view of a loading tube apparatus for facilitating loading into a further sheath of a delivery system.

Referring to FIGS. 5 and 6, a further loading apparatus is illustrated in the form of a loading tube apparatus 120. The loading tube apparatus 120 may generally comprise a plurality of (at least first and second) segments 122a, 122b that are assemble around a portion of a delivery catheter to define a tubular shape or form 122; and at least one retainer for retaining the plurality of segments in the assembled shape. In the illustrated form, the retainer comprises an overtube 124, and a threaded nut 126 that is securable to a mouth of the overtube 124. The segments 122a and 122b enable a tubular form to assembled having an inner diameter that would otherwise be impossible or difficult to slide over a catheter sheath, at least in use. The retainer enables the segments to be secured in position, and can have an inner diameter sufficiently large to be slid on to the catheter.

Figure 7:
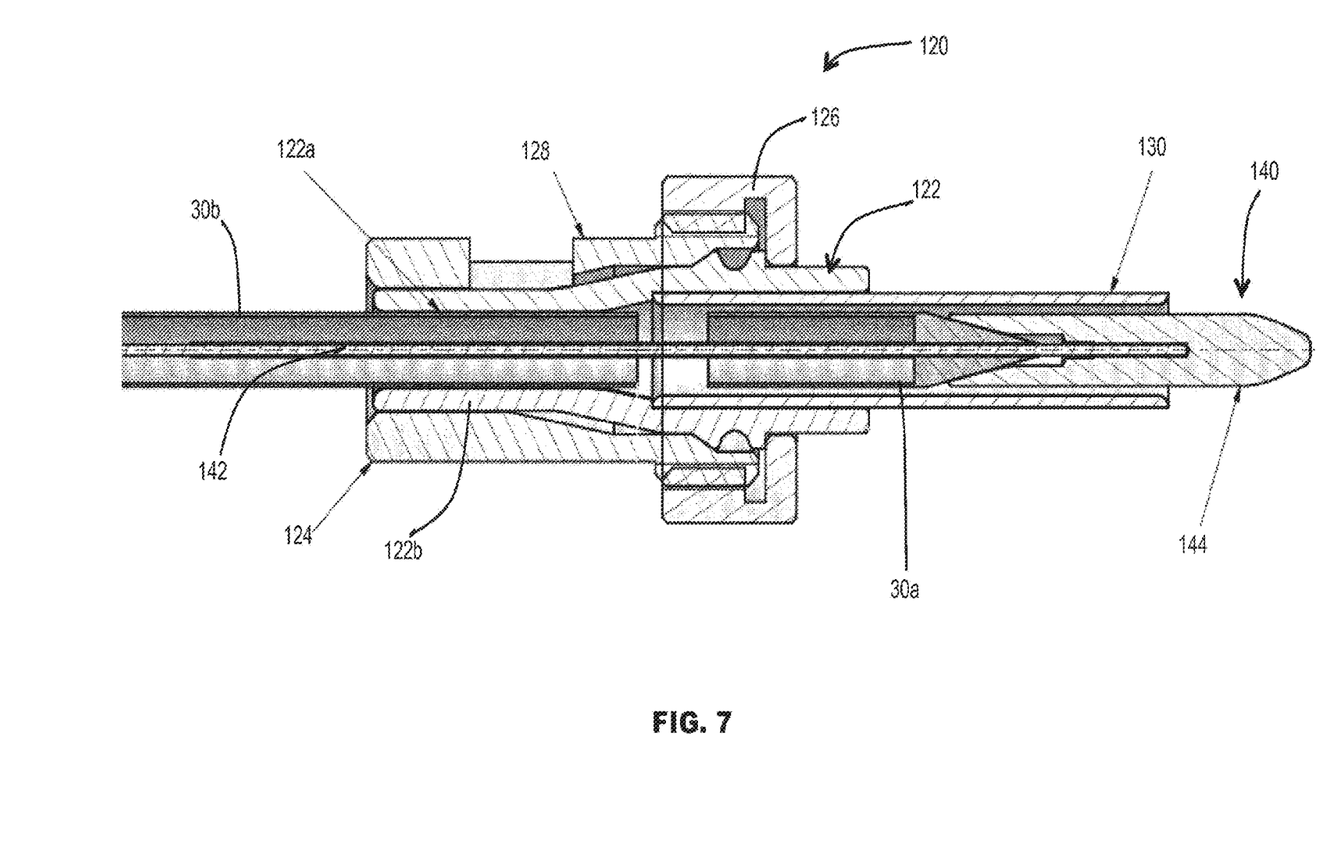
FIG. 7 is a schematic section showing the loading tube apparatus assembled in use.

The tubular form 122 may provided a precisely dimensioned form fit with respect to a sheath of the catheter, for example, with respect to the proximal sheath 30b. The tubular form 122 may reinforce the proximal sheath 30b to enable a portion of the stent-valve 10 to be directed compressed and loaded into the proximal sheath 30b without overstressing the sheath material.

The segments 122a and 122b may of generally transparent material, such as transparent plastics, to enable viewing of the stent within the sheath 30b. The overtube 124 may also be of transparent material and/or may include a viewing window or cut-out 128, to facilitate unhindered viewing while the overtube 124 is in place.

The apparatus 40 and/or 120 may further comprise an intermediate loading tube 130 to further facilitate manipulation of the stent-valve 10, and to assist loading. The loading tube 130 may have a generally cylindrical form, dimension to slide, with a form fit, over the sheaths 30 and 30b. The segments 122 may have a step change in internal diameter (in the region indicated at 132 in FIG. 7) to accommodate the intermediate tube around the sheath.

The apparatus 40 and/or 120 may further comprise an interior support 140 in the form of a metallic tube or shaft 142 insertable into the guidewire lumen of the delivery catheter from the distal end. The shaft may terminate in a plastics handle 144 by which the interior support may be manipulated by hand, and a counter-force applied manually to the distal end of the delivery catheter in use.

There now follows a description of a technique for compressing and loading a stent-valve 10 on to a delivery catheter 12 of FIG. 1. In order to compress and load a stent-valve 10 into a delivery catheter 12, the sheaths 30a and 30b of the delivery catheter 12 are first opened. The stent-valve 10 is loaded into the mouth of the channel 42, the mover 44 placed over the entrance, and secured with the driver 46. The apparatus 40 containing the stent-valve 10 may then be placed over the distal end of the delivery catheter 12, and slid in a proximal direction beyond the distal sheath 30a.

The stent-valve 10 is initially compressed by rotating the driver 46, to advance the stent-valve 10 within the channel 42 in a distal direction with respect to the catheter 12. When the attachment elements of the stent-valve emerge at the exit of the apparatus 40, they may be manually fitted on to the stent-holder of the catheter, optionally using the second compressor stage 102 to further compress or pinch the stent-valve to narrow the attachment elements to mate with the stent-holder.

Thereafter, a portion of the stent-valve 10 is loaded into the first sheath 30a by a sequence of, step-wise: (i) rotating the driver 46 to advance the stent-valve 10; (ii) after rotation of the driver 46 is stopped, operating the crimper to further compress or pinch the portion of the stent-valve 10 at the exit of the apparatus; (iii) sliding the first sheath 30a proximally to cover the newly exposed portion of the stent-valve; (iv) relaxing the crimper; and (v) repeating the steps (i)-(iv) one or more times.

Thereafter, the intermediate loading tube 130 may be slid over the partly compressed stent-valve, from the distal end of the delivery catheter, to further compress the stent-valve.

The apparatus 40 may be removed from the delivery catheter.

Thereafter, the loading tube apparatus 120 can be assembled around the second or proximal sheath 30b, and optionally the intermediate tube 130. The segments 122 are fitted into place, and secured by the overtube 124 and nut 126.

The opposite portion of the stent-valve is loaded into the second sheath 30b by progressively closing the sheath 30b over the respective portion of the stent-valve 10. The interior support 140 may be fitted and used to apply to the distal end of the delivery catheter 10 a counter force to balance the force needed for forcibly translating the second sheath 30b over the stent-valve 10.

During the translation of the second sheath 30b, the loading tube apparatus 120 and the intermediate tube 130 may translate together in unison with the second sheath 30b, to provide continuous support as the sheath 30b moves over the stent-valve 10.

After loading, the loading tube apparatus 120 may be disassembled and removed, the intermediate loading tube 130 removed, and the interior support 140 withdrawn from the distal end of the delivery catheter.

The above components may be made of any suitable material or materials, including metal and/or plastics and/or ceramics. Merely by way of example, the channel 42, the driver 46, the loading tube assembly 120, and the intermediate loading tube 130 may of plastics; and/or the ring 60 of the mover 44 may be of metal; and/or the limbs 56 of the mover 44 may be of plastics (e.g. to avoid metal-metal contact with the stent component 14). In other forms, the limbs 56 could be of metal or ceramics, either optionally being coated or carrying a cover of plastics. Alternatively, the ring 60 and the limbs 56 of the mover 44 could be of plastics, e.g. integrally moulded together.

The loading tube 48 and/or the channel 42 and/or the loading tube apparatus 120 may optionally be transparent or translucent to enable the operator to see the state of the stent-valve 10 during compression, and to aid loading and manipulation of the delivery catheter 12.

The foregoing description is merely illustrative of preferred embodiments of the invention and does not limit the scope of protection. Many equivalents, modifications and improvements may be used within the scope of the invention.

The invention claimed is:

1. An apparatus configured to compress a cardiac stent-valve for loading into a delivery catheter, the apparatus comprising:
   a first compressor stage for compressing a stent-valve,
   wherein the first compressor stage comprises a hollow channel and an advancing member
   wherein the first compressor stage is configured for progressively compressing the stent-valve in response to, or in association with, longitudinal advancement of an advancing member against the stent-valve within the hollow channel; and
   a second compressor stage coupled or couplable to the first compressor stage and configured to further compress a portion of the stent-valve after passing through the first compressor stage and without advancement of the stent-valve within the second compressor stage,
   wherein the first compressor stage and second compressor stage are operated by respective rotary actuators that are rotatable about a longitudinal axis of the apparatus.

2. The apparatus of claim 1, wherein the second compressor stage is releasably coupled at, or to be at, an exit of the first compressor stage.

3. The apparatus of claim 1, wherein the second compressor stage comprises a plurality of movable elements.

4. The apparatus of claim 3, wherein a plurality of movable elements are assembled around a portion of a delivery catheter to define a tubular shape; and further comprising at least one retainer configured to retain the plurality of movable elements in the tubular shape.

5. The apparatus of claim 4, wherein the at least one retainer comprises at least one threaded nut, and/or a supporting overtube.

6. The apparatus of claim 1, wherein the second compressor stage comprises a screw threaded actuator for actuating the second compressor stage.

7. The apparatus of claim 1, wherein the advancing member of the first compressor stage is configured to apply a longitudinal pushing force from radially outside the hollow channel to the stent-valve within the hollow channel.

8. The apparatus of claim 7, wherein the advancing member comprises a ring from which plural limbs project inwardly, the limbs sliding in slots through a wall of the hollow channel.

9. The apparatus of claim 1, wherein the first compressor stage comprises shaped interior surface configured to progressively compress the stent-valve in response to longitudinal advancement of the stent valve within the hollow channel.

10. The apparatus of claim 9, wherein the shaped interior surface has a diameter that reduces progressively along the longitudinal axis of the channel in a direction towards an exit.

11. The apparatus of claim 1, further comprising at least one loading tube removably positionable at the exit of the second compressor stage,
   wherein the loading tube has a bore therein which is equal to or smaller than an exit diameter of the second compressor stage.

12. The apparatus of claim 11, wherein the loading tube comprises a plurality of segments that are assemblable to define a tubular shape.

13. The apparatus of claim 12, further comprising a retainer configured to retain the plurality of segments in the tubular shape.

* * * * *